(12) United States Patent
Kool et al.

(10) Patent No.: US 8,268,977 B2
(45) Date of Patent: Sep. 18, 2012

(54) STRONGLY QUENCHING OLIGOMERIC EXCIMER/QUENCHER PAIRS FOR DETECTION SCHEMES

(75) Inventors: Eric Todd Kool, Stanford, CA (US); James N. Wilson, Coral Gables, FL (US); Nan Dai, Middle Island, NY (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 281 days.

(21) Appl. No.: 12/619,559

(22) Filed: Nov. 16, 2009

(65) Prior Publication Data
US 2010/0129820 A1 May 27, 2010

Related U.S. Application Data

(60) Provisional application No. 61/199,919, filed on Nov. 20, 2008.

(51) Int. Cl.
*C07H 21/00* (2006.01)
*C07H 21/02* (2006.01)
*C07H 21/04* (2006.01)
*C07H 19/04* (2006.01)
*C12Q 1/68* (2006.01)

(52) U.S. Cl. .................. 536/23.1; 536/26.6; 435/6.1

(58) Field of Classification Search ...... 435/6; 536/23.1, 536/26.6
See application file for complete search history.

(56) References Cited

U.S. PATENT DOCUMENTS 6,592,847 B1 * 7/2003 Weissleder et al. ............ 424/9.6
7,423,133 B2 9/2008 Kool et al.
2004/0215012 A1 10/2004 Kool et al.
2008/0213747 A1 9/2008 Jones et al.

OTHER PUBLICATIONS

Cuppoletti; et al., "Oligomeric Fluorescent Labels for DNA", Bioconjugate Chem (2005), 16:528-534.
Jones; et al., "Building highly sensitive dye assemblies for biosensing from molecular building blocks", PNAS (2001), 98(26):14769-14772.
Lu; et al., "Superquenching in Cyanine Pendant Poly(L-lysine) Dyes: Dependence on Molecular Weight, Solvent, and Aggregation", J. Am. Chem. Soc. (2002), 124(3):483-488.
McIntyre; et al., "Development of a novel fluorogenic proteolytic beacon for in vivo detection and imaging of tumour-associated matrix metalloproteinase-7 activity", Biochem. J. (2004), 377:617-628.

(Continued)

*Primary Examiner* — Jezia Riley
(74) *Attorney, Agent, or Firm* — Bozicevic, Field & Francis LLP; Pamela J. Sherwood

(57) ABSTRACT

Compositions and systems are provided for the high efficiency quenching small water-soluble oligomers, or oligofluors, of from about 1-10 kd in size, where the oligofluors comprise multiple excimeric or exciplex forming fluorophores arranged on a scaffold, which are efficiently quenched by a quencher entity linked to the oligomer through a cleavable moiety. Fluorophores of interest include, without limitation, aromatic fluorophores such as pyrenes, e.g. benzopyrene, perylene, pyrene, etc. In some embodiments the oligofluor/quencher combination provides for a Stern-Vollmer constant ($K_{SV}$) of greater than about $10^6$ $M^{-1}$, and may be greater than about $10^7$ $M^{-1}$, greater than about $10^8$ $M^{-1}$, or more. In some embodiments of the invention, the scaffold is a phosphodiester/glycoside backbone, e.g. an analog of a polynucleotide. The system of oligofluors and quenchers can be used in qualitative and quantitative screening and detection methods to detect any enzymatic, chemical or catalytic activity that can cleave the moiety between the quencher and scaffold.

15 Claims, 8 Drawing Sheets

OTHER PUBLICATIONS

Nagase; et al., "Design and Characterization of a Fluorogenic Substrate Selectively Hydrolyzed by Stromelysin 1 (Matrix Metalloproteinase-3)"*, The Journal of Biological Chemistry (1994), 269(33):20952-20957.

Rininsland; et al., "High-throughput kinase assays with protein substrates using fluorescent polymer superquenching", BMC Biotechnology (2005), 5(16), p. 1-6.

Wilson; et al., "Efficient Quenching of Oligomeric Fluorophores on a DNA Backbone", J. Am. Chem. Soc. (2007), 129 (50):15426-15427.

Wilson; et al., "Oligodeoxyfluorosides: Strong Sequence Dependence of Fluorescence Emission", Tetrahedron (2007), 63(17):3427-3433.

Xia; et al., "Applications of Fluorescent Polymer Superquenching to High Throughput Screening Assays to Protein Kinases", ASSAY and Drug Development Technologies (2004), 2(2):183-193.

* cited by examiner

A

B

C

STRONGLY QUENCHING OLIGOMERIC EXCIMER/QUENCHER PAIRS FOR DETECTION SCHEMES

GOVERNMENT RIGHTS

This invention was made with Government support under contracts NIHGM067201 and NIHF32GM075697 awarded by the National Institutes of Health. The Government has certain rights in this invention.

BACKGROUND OF THE INVENTION

Fluorescence based sensors provide sensitive means of determining the presence of compounds of interest in a sample. Sensors may include a source of fluorescence signal, and a substrate for chemical or biocatalytic transformation. Various signal transduction methodologies can be use in measuring the response, where the sensor can produce a detectable change in fluorescence upon interacting with an analyte. Fluorescent sensors can provide desirable properties such as water solubility, low detection limits, and high selectivity for a desired analyte, where the analyte can be a small molecule, an enzyme, a catalytic metal, and the like.

Fluorescence quenching provides a useful tool in sensor design (Haugland, R. P. Handbook of Fluorescent Probes and Research Products, Ninth Edition; Molecular Probes: Eugene, Oreg., 2002). Over the past years, organic dyes have been used extensively, for example in FRET applications, but the requirements of FRET make matching a donor-acceptor pair difficult. (Lakowicz, J. R. Principles of Fluorescence Spectroscopy, 2nd ed.; Kluwer Academic: New York, 1999).

As a result of the greatly expanding use of fluorescent labels in research and diagnostic applications, there is a corresponding increase in the need for very low background, for example as provided in a highly quenched fluorophore-quencher pair. The present invention addresses this need. It provides a class of fluorophores that can be exceptionally strongly quenched. Moreover, it provides pairings of quenchers with these fluorophores that yields this very low background fluorescence, and provides a specific structural design of sensor molecules that include these fluorophores and quenchers. Further, it provides uses for detection of a variety of analytes and conditions.

Publications

Wilson et al. (2007) J.A.C.S. 129:15426-15427 describe the efficient quenching of oligomeric fluorophores on a DNA backbone. Wilson et al. (2007) Tetrahedron 63(17):3427-3433 describe how fluorescent nucleobases can interact electronically to yield complexity in fluorescence emission. Cuppoletti et al. (2005) Bioconjug Chem. 16(3):528-34 describe oligomeric fluorescent labels for DNA. Kool et al. in U.S. Pat. No. 7,423,133 describes fluorescent glycosides and methods for their use. Each publication is herein specifically incorporated by reference.

Nagase et al. (1994) J.B.C. 33:20952-20957; and McIntyre et al. (2004) Biochem J. 377:617-628 teach fluorescently labeled protease sensing molecules with a fluorophore at one end and a quencher at the opposite end. Protease enzymes cleave the peptides, separating the quencher from the fluorophore. The increase in fluorescence is about 11 to about 17 fold, with substantial background fluorescence.

Jones et al., U.S. Patent Application 20080213747 describe fluorescent polymers and their use in superquenching-based bioassays. Jones et al. (2001) PNAS 98(26):14769-72 investigates fluorescence superquenching for polyelectrolytes consisting of cyanine dye pendant polylysines ranging in number of polymer repeat units (N(PRU)) from 1 to 900, both in solution and after adsorption onto silica nanoparticles. Lu et al. (2002) JACS 124:483-488 describe superquenching in cyanine pendant poly(l-lysine) dyes. Applications of fluorescent polymer superquenching to high throughput screening assays for protein kinases is discussed by Xia et al. (2004) Assay Drug Dev Technol. 2(2):183-92.

SUMMARY OF THE INVENTION

Compositions and systems are provided for the high efficiency quenching of fluorescence molecules. The fluorescent molecules are small water-soluble oligomers (oligofluors) comprising excimeric or exciplex forming fluorophores arranged on a backbone; which are efficiently quenched by a quencher linked to the oligomer through a cleavable moiety. The sensor molecules comprise an oligofluor linked to a quencher through a cleavable moiety. In some embodiments of the invention, the backbone is a DNA analog, for example a phosphodiester backbone, phosphorothioate backbone, peptide nucleic acid, etc. In other embodiments the backbone is a polypeptide backbone. The sensor system can be used in qualitative and quantitative screening and detection methods.

BRIEF DESCRIPTION OF THE DRAWINGS

The following figures form part of the present specification and are included to further demonstrate certain aspects of the present invention. The invention may be better understood by reference to one or more of these figures in combination with the detailed description of specific embodiments presented herein.

U/mg (Fluka 62298); PCL: Lipase from *Pseudomonas cepacia*, 46.2 U/mg (Fluka 62309); PFL: Lipase from *Pseudomonas fluorescens*, 35.2 U/mg (Fluka 95608); RAL: Lipase from *Rhizopus arrhizus*, 10.5 U/mg (Fluka 62305); RNL: Lipase from *Rhizopus niveus*, 4.49 U/mg (Fluka 62310); HPL: Lipase from hog pancreas, 30.1 U/mg (Fluka 62300); ANL: Lipase from *Aspergillus niger*, 184 U/g (Fluka 62301).

Figure 5A:
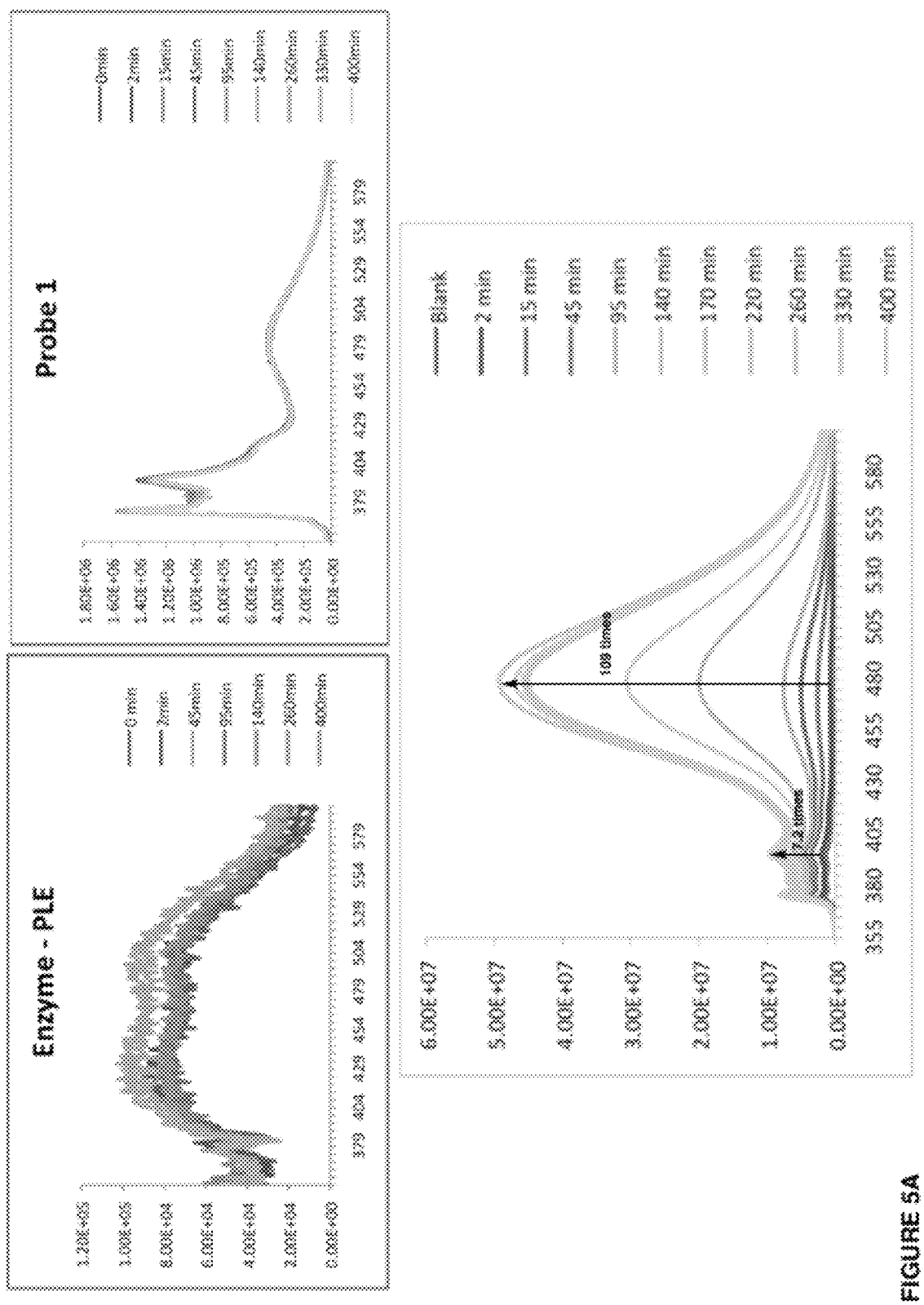
Figure 5B:
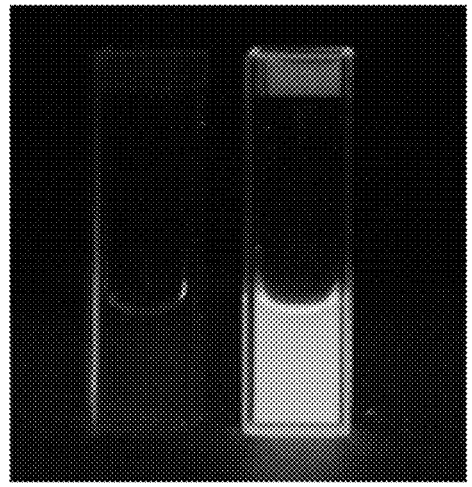

FIG. 5A-5B. Photograph of probe 1 in water for 3 days (FIG. 5A) and after treatment with porcine liver esterase (FIG. 5B).

Figure 6:
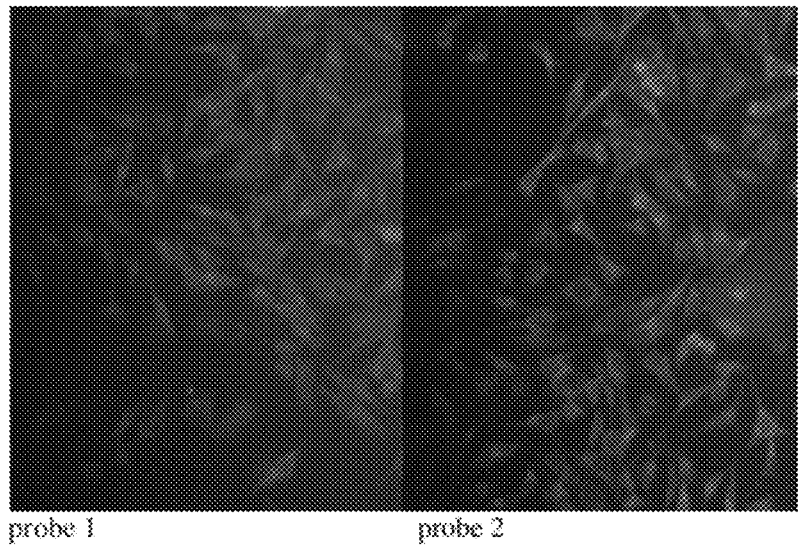

FIG. 6. Probes 1 and 2 were tested for the ability to report on cellular esterase activity. We incubated probes at 5 µM with HeLa cells for 24 hr, washed the cells and took a photomicrograph.

DETAILED DESCRIPTION OF THE EMBODIMENTS

Compositions and systems are provided for the high efficiency quenching small water-soluble oligomers, or oligofluors, of from about 1-10 kd in size, where the oligofluors comprise multiple excimeric or exciplex forming fluorophores arranged on a backbone, which are efficiently quenched by a quencher entity linked to the oligomer through a cleavable moiety. Fluorophores of interest include, without limitation, aromatic fluorophores such as pyrenes, e.g. benzopyrene, perylene, pyrene, etc.

In some embodiments the oligofluor/quencher combination provides for a Stern-Vollmer constant ($K_{SV}$) of greater than about $10^6$ $M^{-1}$, and may be greater than about $10^7$ $M^{-1}$, greater than about $10^8$ $M^{-1}$, or more. When the oligofluor and quencher are combined in a sensor of the present invention, the compositions provide for an increase in fluorescence, following cleavage of the quencher, of at least about 20-fold, at least about 50-fold, at least about 100-fold; at least about 1000-fold, at least about $10^5$ fold, at least about $10^6$-fold or more.

In some embodiments of the invention, the scaffold is a phosphodiester/glycoside backbone, e.g. an analog of a polynucleotide. The sensor system of can be used in qualitative and quantitative screening and detection methods to detect any enzymatic, chemical or catalytic activity that can cleave the moiety between the quencher and scaffold.

The fluorophores are generally attached to contiguous backbone residues, i.e. the fluorochromes to be quenched are not separated by backbone groups lacking a fluorochrome.

The relevant art for the invention includes molecules having a single fluorescent dye conjugated to a fluorescence quenching group via chemical structure that can be cleaved. An example is existing protease sensor molecules in which the fluorophore and quencher are linked with peptide bonds in between; cleavage results in an increase in fluorescence, for example as described by McIntyre et al., supra, or Nagase et al., supra. A limitation of this type of sensor is low signal-to-noise ratios. The quenching is not perfect, and so the signal increase may be on the order of about a 10-fold increase. As a result, a true sensing of the bond-cleaving activity cannot be distinguished from unreacted probes at ten times the concentration. Thus it is difficult to detect small amounts of activity, especially in samples where levels of activity are unknown.

In contrast, the compositions of the present invention, in which multiple excimer or exciplex forming dyes are linked to a single quencher, yield highly efficient quenching, from 20-fold to 1,000,000-fold or more. This leads to much higher sensitivity for detection of lower levels of activity, and yielding much greater utility in unknown samples.

Unlike the prior art compositions, the compositions of the present invention utilize multiple fluorophores linked to a single quencher. It is not obvious from the current art that this would yield better signal-to-noise. Indeed, one might expect the opposite: a single quencher might not be able to quench more than one dye as well as it quenches one. Moreover, multiple dyes often quench each other, again leading to low fluorescence.

Another feature of the invention is the use of dyes that display an excimer or exciplex type of fluorescence. Prior to the present invention it was not obvious that excimer/exciplex-forming dyes would be quenched more efficiently than non-excimer dyes. In some instances the art has expressly taught away from the use of excimers in fluorescent polymer sensors because the interchain interactions (forming excimers) were believed to lead to low fluorescence. The only previously known type of interaction between dyes that leads to strong quenching is the "J-aggregate" interaction. Lu et al., supra, describe cyanine pendant poly(l-lysine) dyes, which are polymer mixtures of variable length, unlike the well-defined single molecular structures of the present invention. These polymers rely on "J-aggregate" interaction between cyanine dyes, rather than an excimer/exiplex mechanism. The J-aggregate mechanism results in low quantum yields, of 0.9% to 2.7%. In contrast, the excimer/exciplex oligofluors of the present invention have quantum yields of at least about 10%, at least about 15%, at least about 20%, at least about 25% or more, and thus are much brighter than those described by Lu et al.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing those components that are described in the publications that might be used in connection with the presently described invention.

As used herein, compounds which are "commercially available" may be obtained from standard commercial sources including Acros Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Ill.), Riedel de Haen A G (Hannover, Germany), Spectrum Quality Product, Inc. (New Brunswick, N.J.), TCI America (Portland Oreg.), Trans World Chemicals, Inc. (Rockville Md.), Wako Chemicals USA, Inc. (Richmond Va.); Molecular Probes (Eugene, Oreg.); Applied Biosystems, Inc. (Foster City, Calif.); and Glen Research (Sterling, Va.).

As used herein, "suitable conditions" for carrying out a synthetic step are explicitly provided herein or may be discerned by reference to publications directed to methods used in synthetic organic chemistry. The reference books and treatise set forth above that detail the synthesis of reactants useful in the preparation of compounds of the present invention, will also provide suitable conditions for carrying out a synthetic step according to the present invention.

As used herein, "methods known to one of ordinary skill in the art" may be identified though various reference books and databases. Suitable reference books and treatise that detail the synthesis of reactants useful in the preparation of compounds of the present invention, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Specific and analogous reactants may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services.

"Stable compound" and "stable structure" are meant to indicate a compound that is sufficiently robust to survive isolation to a useful degree of purity from a reaction mixture, and formulation into an efficacious therapeutic agent.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution. The term lower alkyl will be used herein as known in the art to refer to an alkyl, straight, branched or cyclic, of from about 1 to 6 carbons.

The compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as, their racemic and optically pure forms. Optically active (+) and (−), (R)- and (S)-, or (D)- and (L)-isomers may be prepared using chiral synthons or chiral reagents, or resolved using conventional techniques, such as reverse phase HPLC. When the compounds described herein contain olefinic double bonds or other centers of geometric asymmetry, and unless specified otherwise, it is intended that the compounds include both E and Z geometric isomers. Likewise, all tautomeric forms are also intended to be included.

Compositions

Sensors of interest for the methods and systems of the invention have the structural formula:

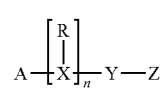

I wherein A may be present or absent. Where A is present it may be a backbone group, or a bond or linker to a substrate, which substrate may include a bead, polynucleotide, polypeptide, solid surface, etc.;

X is a backbone group;

R is an excimer or exciplex forming dye, where each R can be the same or different;

n is 2 to 20,

Y is a cleavable linker, and

Z is a quencher for the exciplex/excimer of R.

The portion of the sensor excluding the cleavable linker and quencher may be referred to herein as an "oligofluor".

The fluorochrome R may be one or a combination of fluorochromes, wherein R is a fluorochrome, where each R can be the same or different, and wherein at least two R groups are an excimer or exciplex forming monomer. Excimer- or exciplex-forming monomers include pyrene, perylene, benzopyrene, oxoperylene, rubrene, perylene bisimide, styrene, anthracene, tetracene, pentacene, and fluorene. R may additionally be phenanthrene, stilbene, dimethylaminostilbene, quinacridone, fluorophenyl-dimethyl-BODIPY, bis-fluorophenyl-BODIPY, acridine, terrylene, sexiphenyl, porphyrin, phenylporphyrin, (fluorophenyl-dimethyl-difluoroboradiaza-indacene)phenyl, (bis-fluorophenyl-difluorobora-diaza-indacene)phenyl, quaterphenyl, bi-benzothiazole (multiple isomers possible), ter-benzothiazole, bi-naphthyl, bi-anthracyl (multiple isomers possible), and ter-naphthyl (multiple isomers possible).

R is linked to the scaffold by any convenient linkage that preserves the fluorescent and excimeric properties of the fluorochrome, for example a C—C bond between an annular carbon of the aromatic group, and a sugar. Where the backbone is a polynucleotide backbone, R may be linked, for example, as a C—C bond between the fluorochrome and the C1 position of the sugar. Where the backbone is a polypeptide, R may be linked, for example, as a C—C bond between the fluorochrome and the alpha or beta carbons of alanine, or another small amino acid.

The cleavable linker, Y, comprises a linkage that is cleaved by an analyte of interest, where the analyte may be an enzyme, e.g. esterase, lipase, nuclease, glycosidase, peptidase; a catalyst, e.g. platinum, palladium, etc., or an environmental condition, e.g. a reducing environment, an oxidizing environment, etc. The primary requirement for Y is that it be stable to storage conditions and control samples, but labile in the presence of the analyte of interest. Y may be tailored to the analyte, e.g. a nucleotide sequence that is susceptible to a specific nuclease; or a peptide that is susceptible to a specific peptidase. For example, different types of esterases prefer different substrates, e.g. aryl esters or alkyl esters, longer ester chains versus shorter ones. These preferences are known in the art. The length of the linker Y may be tailored to optimize the interaction of the quencher and the exciplex.

In some embodiments of the invention, the cleavable linker Y comprises a chain of less than about 50 atoms in length, for example, less than about 40 atoms in length, less than about 30 atoms in length, less than about 25 atoms in length, less than about 20 atoms in length, less than about 15 atoms in length, or less than about 10 atoms in length; where the chain comprises a cleavable bond; and one or more of an amide, a thioether and a triazole. In some embodiments of the invention, the chain comprises a group formed as the result of a bioconjugation reaction between two reactive groups such as is described by G. T. Hermanson in "Bioconjugate Techniques", 1996, Academic Press, which is herein incorporated by reference.

In some embodiments of the invention, the cleavable linker Y is of the structure:

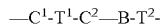

where $C^1$ and $C^2$ are each independently a chain of about 2 to 6 atoms in length;

where $T^1$ is selected from a thioether group, a triazole group, and an amide group;

where $T^2$ is selected from a single bond, a chain of about 2 to 6 atoms in length, an aminomethylene group, an aminomethylphenyl group, and a benzyl group; and where B is a cleavable bond.

The quencher, Z, is selected to have high quenching for the oligofluor, where the oligofluor/quencher pair have a Stern-Volmer constant ($K_{SV}$) of greater than about $10^6$ $M^{-1}$, and may be greater than about $10^7$ $M^{-1}$, greater than about $10^8$ $M^{-1}$. The quenching follows a conventional "Stern-Volmer" relationship: $\phi^\circ/\phi=1+K_{SV}[MV^{2+}]$ where $\phi^\circ$ and $\phi$ are the quantum efficiencies (or intensities) of fluorescence in the absence and presence of $MV^{2+}$, respectively, and $[MV^{2+}]$ is the $MV^{2+}$ concentration.

Quenchers of interest include, without limitation, methyl viologen, methyl red, dabcyl, dabsyl, dansyl, FRET acceptors, TAMRA, Iowa black, nitroxyl quenchers, black hole quenchers, dimethylaminostilbene, dimethylaminoazobenzene, dimethylaniline, nitrobenzene, pentafluorobenzene, methylpyridinium, and phenyl-(methylpyridinium) and the like. Specific examples of fluorescence quenching nucleoside analogs include dimethylaminostilbene deoxyriboside; dimethylaminoazobenzene deoxyriboside; dimethylaniline deoxyriboside; nitrobenzene deoxyriboside; pentafluorobenzene deoxyriboside; methylpyridinium deoxyriboside; and phenyl-(methylpyridinium) deoxyriboside.

X is a backbone group, or scaffold, which optionally comprises a polar moiety, e.g. a phosphodiester linkage. X groups of interest are capable of linking together to form an oligomeric backbone. Such groups include amino acids, phosphodiesters, phosphorothioate, phosphotriester, locked nucleic acid (LNA), morpholino, 2'-O-methyl RNA; peptide nucleic acid, acrylamides, amides, saccharides, etc.

In some embodiments X is a phosphodiester backbone group where the phosphodiester backbone group comprises a phosphodiester linkage and a sugar moiety, where the sugar can be a hexose (allose, altrose, glucose, mannose, gulose, idose, galactose, or talose) or a pentose (ribose, arabinose, xylose, or lyxose). The sugar can be in a reduced form such as in 2-deoxyribose or 3-deoxyribose. The C1 position of the sugar moiety can generally be attached to any available position on the aromatic hydrocarbon group, and can be an alpha isomer or beta isomer.

An oligofluor may comprise a homogenous R group, or may comprise R groups independently selected from the fluorophores recited herein. In some embodiments, n is from 2-20, from 4-16, from 4-8, etc., where each R group is an excimer-forming fluorophore, e.g. pyrene. In some embodiments, X is a phosphodiester backbone, where n is from 2-20, from 4-16, from 4-8, etc., and each R group is an excimer fluorophore, e.g. pyrene. Examples of such oligomers include, without limitation:

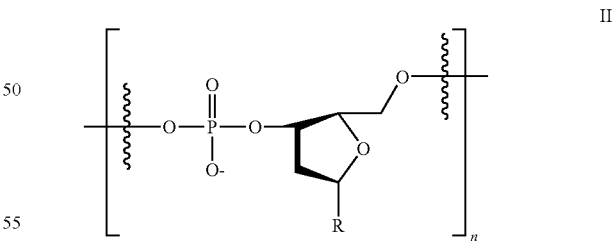

II where R is an aromatic fluorochrome, including without limitation, pyrenes, and where n is from 2-20, usually from 4-16, from 4-8, etc. The attaching bond to deoxyribose is in either the alpha or beta configuration.

The oligofluors can have absorbance maxima of about 250 nm to about 1000 nm, and more preferably about 300 nm to about 700 nm, and fluorescence emission maxima of about 300 nm to about 1200 nm, and more preferably about 350 nm to about 900 nm. The molar absorptivities can be about $1\times10^2$ $Lmol^{-1}$ $cm^{-1}$ to about $5\times10^8$ $Lmol^{-1}$ $cm^{-1}$, and more preferably about $1 \times 10^3$ Lmol$^{-1}$ cm$^{-1}$ to about $1 \times 10^7$ Lmol$^{-1}$ cm$^{-1}$. The individual Stokes shifts can be about 10 nm to about 300 nm, and more preferably about 20 nm to about 200 nm. The quantum yields in air-saturated methanol can be about 0.001 to about 1.00, and more preferably about 0.1 to about 1.0.

The linker A may be any convenient bond or moiety to join the sensor system to a substrate, molecule for detection, etc.

In some embodiments of the invention, the sensor is conjugated to a substrate through the linker A, where the substrate may be, e.g. a solid surface which may be planar or non-planar, and which may include beads, multi-well plates, sheets, slides, and the like.

In other embodiments the sensor is conjugated to a molecule of interest for detection through the linker A, where the molecule of interest may be, e.g. a polynucleotide probe, ligand, peptide, protein, carbohydrate, etc., where the oligofluor is conjugated to one member of a specific binding pair. Such binding pairs comprise one member that has specific affinity for a complementary member, as compared to diverse other types of molecules.

Specific binding pairs include a wide variety of molecules, which may be arbitrarily called ligands and receptors. For the subject invention, the ligands and receptors may include a wide variety of proteins, such as antibodies, specific binding proteins, such as surface membrane protein receptors, lectins, blood proteins, and the like, carbohydrates, small organic molecules, both naturally occurring and synthetic to which proteins specifically bind, either naturally occurring protein receptors or antibodies, nucleic acids which may hybridize or specifically bind to an homologous or partially homologous sequence usually having at least about 30% complementarity, preferably at least about 50% complementarity over the complementary region, and the like. In effect, any two molecules which have a specific binding affinity may be employed, so that the label may be used for detection of the presence of the complementary member. The desired specificity may be varied widely, depending upon the particular nature of the molecules to be detected, the information desired about the nature of the sample, or the like.

Methods of Detection

Analytes are detected by combining a sensor of the invention having a cleavable bond that is susceptible to cleavage by the analyte, with a test sample suspected of comprising the analyte of interest. Where the analyte is present, Y is cleaved, releasing the quencher from the oligofluor. The change is fluorescence is detected by any convenient method, as known in the art. Reference samples of known analyte composition may be included in an assay, or used to establish reference curves. Typically positive and negative controls are included. Analytes of interest for analysis include any molecule or condition with the capability of cleaving, directly or indirectly, the linker between the oligofluor and quencher.

The analytes are conveniently added in solution, or readily soluble form to the sensor, which may be provided in solution or bound to a substrate, such as a plate, well, bead, fiber, etc. A plurality of assays may be run in parallel with different analyte concentrations to obtain a differential response to the various concentrations. As known in the art, determining the effective concentration of an analyte typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the analyte or at or below the concentration of analyte that does not give a detectable change in fluorescence.

In some assays the analyte is a binding partner of a substrate linked to the sensor, where the binding partner conjugate is brought into contact with the analyte, e.g. in a hybridization reaction, antibody binding reaction, etc. In such assays the unbound binding partner may be washed from the sample, and the presence of the bound binding partner detected by cleaving the linker Y with any appropriate catalyst, enzyme, etc.

For example, the sensor of the invention may be bound to an oligonucleotide probe, which is hybridized to a sample of interest, e.g. microarray, northern blot, tissue section, etc., under conditions permissive for specific hybridization. The excess probe is washed from the sample, and Y cleaved to release the quencher and permit fluorescence.

A further embodiment of the invention is directed towards antibodies covalently attached to one or more of the above described sensors, and methods for their use. The antibodies can be covalently attached to the sensors using any compatible chemical reaction strategy, such as reaction of antibody lysine amines with aldehyde, carboxylate, or isothiocyanate derivatives of oligofluors, or cysteine thiols with thiol, iodoacetyl, or maleimido derivatives of oligofluors. The labelled antibodies can be used in bioassays such as Western blots, dot blots, and ELISA assays. The antibodies can also be used for in vitro applications.

EXPERIMENTAL

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the scope of the invention.

Example 1

Efficient Quenching of Oligomeric Fluorophores on a DNA Backbone

Here we describe the finding of highly efficient quenching in a different class of oligomeric reporters in which the fluorophores are assembled on a DNA backbone. The molecules are well-defined, relatively small, water-soluble oligomers and are trivial to conjugate to DNA. We find that they can display quenching efficiencies that are unprecedented for discrete organic molecules and rival values previously seen only for conjugated polymeric systems.

We have recently studied these DNA-like fluorophores (oligodeoxyfluorosides (ODFs)) as a new class of reporters and sensors (Chart 1). They display highly diverse and tunable properties depending on length, composition, and sequence. To begin to explore the quenching properties of such fluorophores, we constructed a simple oligomer series containing pyrene nucleoside monomers (see structures) to explore the effect of chain length on the optical properties. It is known that pyrene molecules can interact, depending on their orientation and proximity, exhibiting spectral changes both in the ground state and in the excited state.

Chart 1. Structures of Fluorophore Nucleoside Monomers in Sequence 1-14[a]

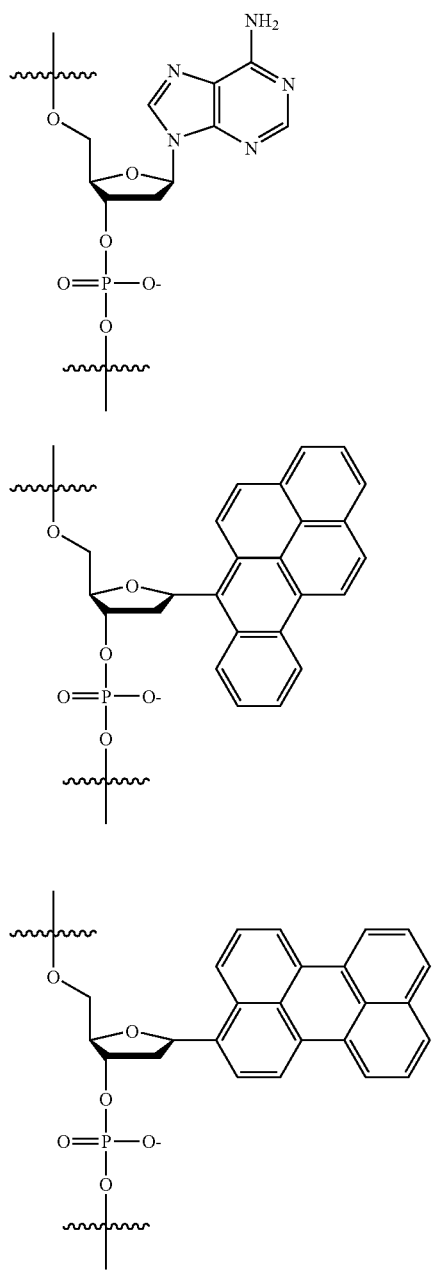

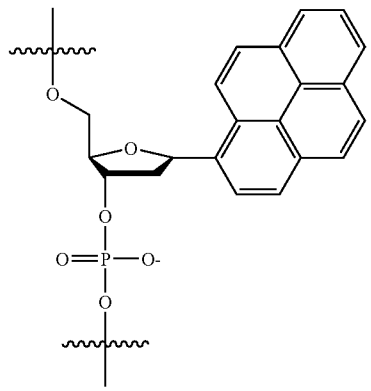

[a]Specific sequences are detailed in Table 1.

Figure 1:
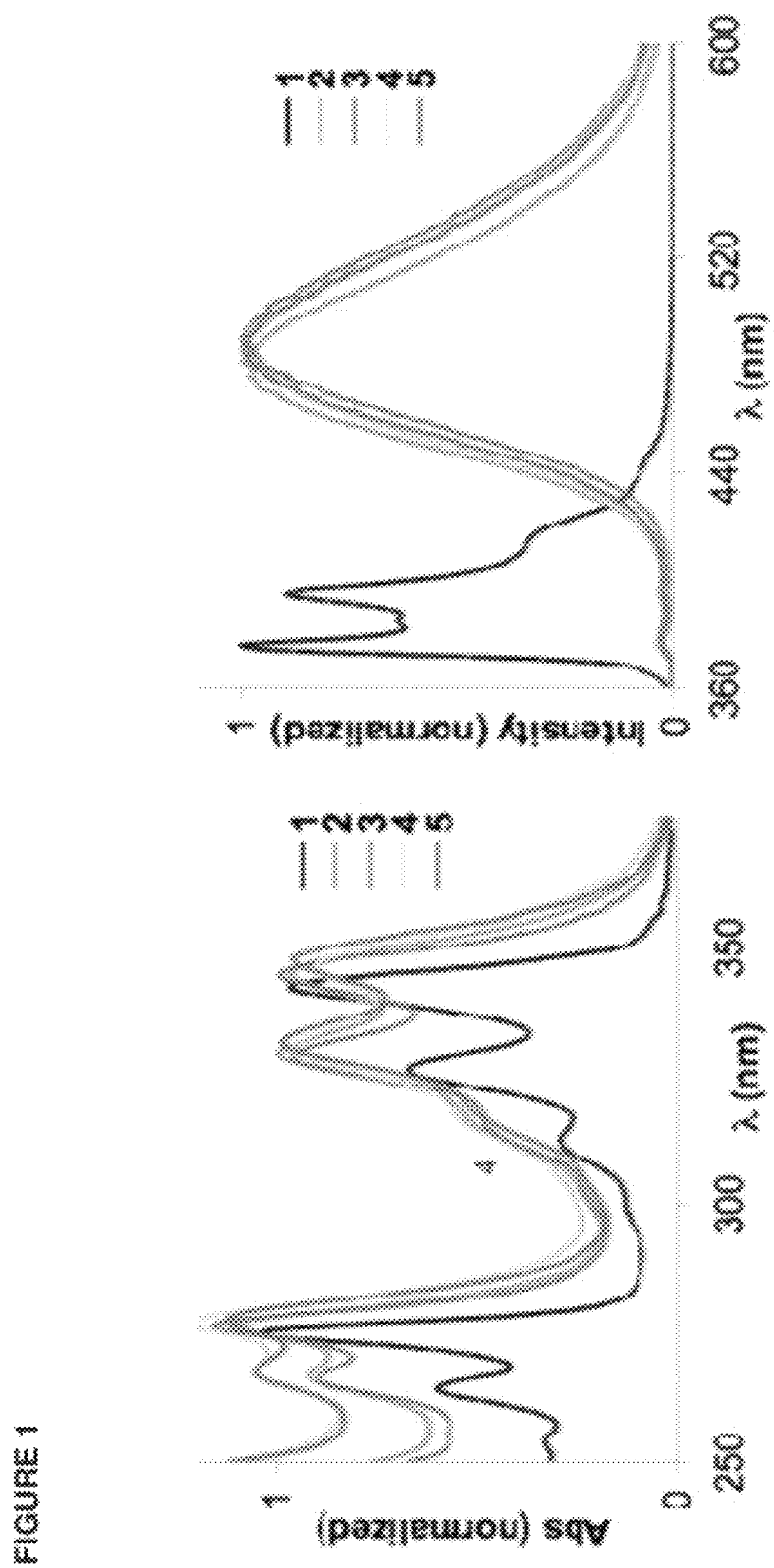
FIG. 1. Absorption (left) and emission (right) spectra of 1-5. The significant spectral broadening in the absorption spectra as well as a broad, red-shifted emission of 2-5 relative to 1 is indicative of both ground-state and excited-state electronic interactions in the sequences containing multiple pyrene moieties.

On the basis of the structure of DNA itself, the deoxyribosephosphate backbone of ODFs is expected to bring appended pyrenes into close contact. We found that the absorption spectra of the oligomers 2-5 (FIG. 1, Table 1) showed clear spectral broadening and a shift to lower energies when compared to the monomer 1. Thus, neighboring pyrenes in 2-5 are not only in close proximity because of restrictions of the DNA backbone, but evidence suggests that they interact electronically in the ground state. Similarly, we found that the pyrene oligomers interact in the excited-state as well: the emission spectrum of 1 shows the expected well-defined vibronic structure with peaks at 376 and 396 nm, while the emission spectra of oligomers 2-5 exhibit a broad, featureless peak centered at 490 nm that can be ascribed to emission of excited-state dimers (excimers) of pyrene (FIG. 1). This interaction is uniform across the series with a ratio of excimer emission to monomer emission of 30:1 or greater (FIG. 1). Quantum yields for the molecules in the series ranged from 0.28 for 1 to 0.15 for 4.

We exposed 1-5 in aqueous buffer to methyl viologen (MV), which has previously been employed as a quencher of fluorescent conjugated polymers, DNA labels and pyrene derivatives. MV was found to quench the emission of 1-5 with Stern-Volmer constants ($K_{SV}$) ranging from $1.9 \times 10^3$ to $4.7 \times 10^6$. In the case of the monomeric pyrene, 1, $K_{SV}$ $1.9 \times 10^3$, which is comparable to other small molecule fluorophore-quencher interactions. However, the octamer (5) was quenched far more efficiently, with a value ($K_{SV}$) $4.7 \times 10^6$ comparable to those for conjugated polymers of much greater length. Thus its quenching is exceptional for a well-defined, relatively small molecule.

TABLE 1

Optical Data for Oligomeric Fluorophores 1-14 in Water[a]

| compd | sequence | abs, $\lambda_{max}$ (nm) | em, $\lambda_{max}$ (nm) | $\Phi_{em}$ | $K_{SV}(M^{-1})$ | comment |
|---|---|---|---|---|---|---|
| 1 | Y | 342, 326 | 376, 396 | 0.28 | $1.9 \times 10^3$ | |
| 2 | $Y_2$ | 345, 329 | 485 | 0.27 | $1.3 \times 10^4$ | |
| 3 | $SY_3S$ | 345, 329 | 492 | 0.21 | $2.2 \times 10^5$ | |
| 4 | $SY_4S$ | 346, 330 | 490 | 0.15 | $5.9 \times 10^5$ | |
| 5 | $S_2Y_8S_2$ | 348, 332 | 490 | 0.16 | $4.7 \times 10^6$ | |
| 6 | $S_2BY$ | 404, 346 | 415, 495 | — | $2.5 \times 10^4$ $1.1 \times 10^5$ | monomer + exciplex |
| 7 | $S_3BYE$ | 452, 346 | 451, 475 | — | $2.1 \times 10^5$ $8.3 \times 10^5$ | monomer + exciplex |
| 8 | AYA | 348, 332 | 380, 399 | 0.43 | $2.4 \times 10^3$ | |
| 9 | $A(YA)_2$ | 348, 332 | 380, 486 | 0.23 | $8.5 \times 10^3$ | |
| 10 | $A(YA)_3$ | 348, 332 | 380, 487 | 0.21 | $3.7 \times 10^4$ | |
| 11 | $A(YA)_4$ | 348, 332 | 381, 487 | 0.20 | $6.1 \times 10^4$ | |
| 12 | $Y_4$ | 348, 333 | 481 | — | $1.2 \times 10^7$ | aggregate |
| 13 | $Y_6$ | 350, 333 | 465, 485 | — | $2.0 \times 10^8$ | aggregate |
| 14 | $Y_8$ | 350, 334 | 466 | — | $8.9 \times 10^8$ | aggregate |

[a] All oligomers were prepared as 3' phosphates; S = THF spacer.

Figure 2:
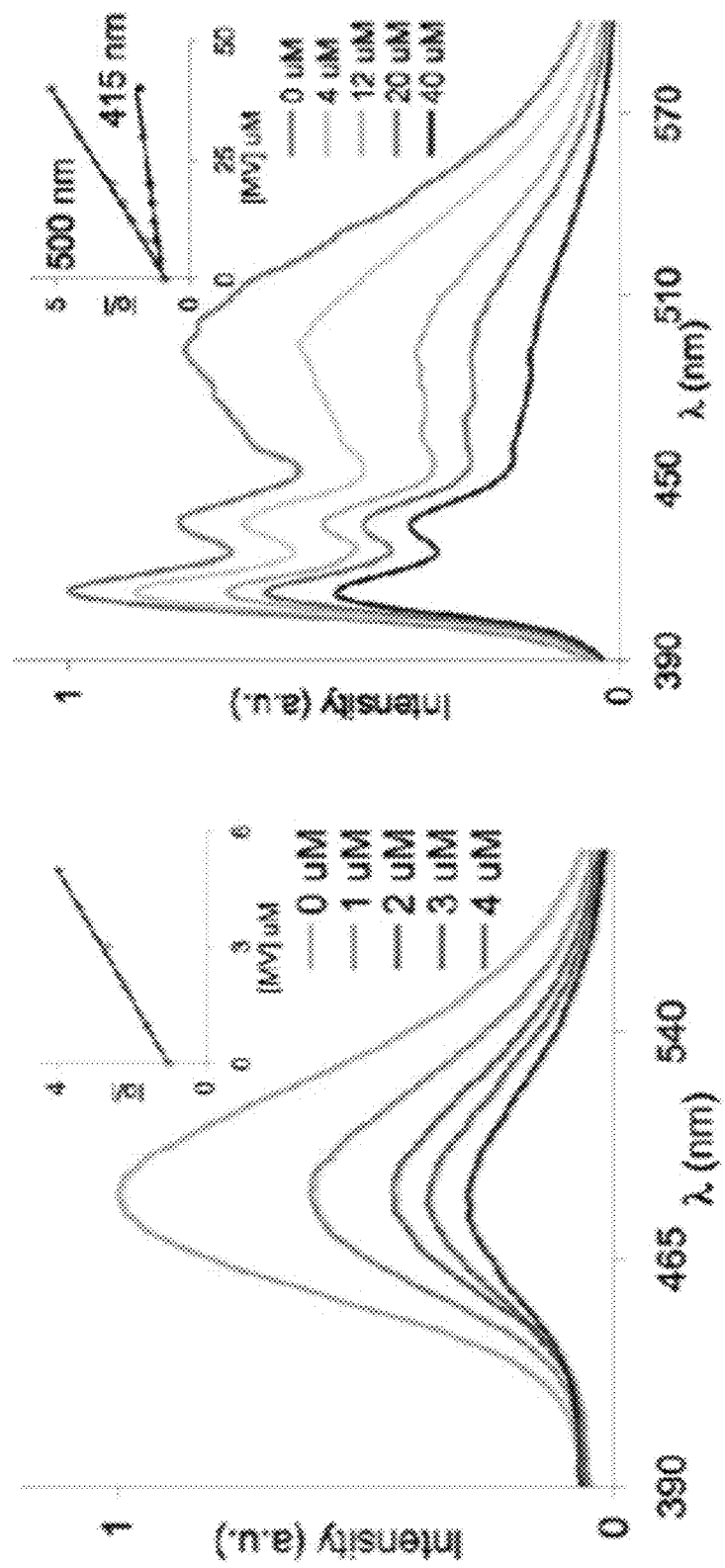
FIG. 2. Fluorescence emission quenching of 4 (left) and 6 (right) by methyl viologen at varying concentrations in water. Insets show Stern-Volmer plots. In the case of 6, greater sensitivity toward quenching is seen for the exciplex emission at 500 nm than for the 415 nm band.

Subsequent experiments showed that efficient quenching is not specific to oligomers of pyrene and can be observed with other δ-stacking fluorophores. Sequences containing benzopyrene and perylene in addition to pyrene (6, 7) demonstrated fluorescent excited-state complexes (exciplexes) that were also highly sensitive to quenching by MV (Table 1). Significantly, in cases where both monomer and exciplex emission was present, the delocalized exciplex emission was much more efficiently quenched. For example, in the case of 6 the long wavelength emission resulting from the interaction of benzopyrene and pyrene was quenched 4-fold more efficiently than the emission of benzopyrene alone (FIG. 2). This result suggested that the delocalized excited state in these stacked fluorophores is more sensitive to quenching by MV than are the emissions from the single fluorophore components.

To gather more evidence as to the influence of the stacked electronic interactions in this efficient quenching, a second series of oligomers (8-11) was constructed with adenine interspaced between pyrene residues. These compounds were designed to separate neighboring pyrenes from each other, thus inhibiting ground and excited-state pyrene-pyrene interactions without inhibiting monomeric pyrene emission. As is evident from the absorption spectra, less ground-state electronic coupling is seen in the A-spaced series with the spectra of 8-11. Similarly, the emission spectra in this series show a combination of pyrene monomer and excimer bands, confirming a lessening of excited state delocalization. Quenching experiments with MV revealed that these adenine-spaced sequences were less efficiently quenched than nonspaced cases, with $K_{SV}$ values approximately one order of magnitude less than for oligomers 2-4 containing the same number of pyrenes. For longer pyrene oligomers (e.g., 12-14) containing no solubilizing spacers, evidence for intermolecular aggregation with δ-stacking was seen, and interestingly, these were quenched with even higher efficiency than the nonaggregated cases, with exceptionally high $K_{SV}$ values of ~$10^7$ to $10^9$.

On the basis of these early data we suggest two possible factors that may contribute to this efficient quenching. First, if the excited state in a multifluorophore stack is mobile (as is the case for conjugated polymers), then collision of a quencher anywhere in the oligomeric fluorophore may cause quenching. This is consistent both with our observation of enhanced quenching of the excimer/exciplex bands over monomer emission and with the long excited states of these delocalized emissions. Second, it is likely that the MV quencher, which is dicationic, has substantial noncovalent binding affinity for these polyanionic molecules; such association may increase the likelihood of quenching as well. Preliminary data at varied ionic strength are supportive of an electrostatic component to the quencher association.

In conclusion, we have found that oligomeric DNA-scaffolded fluorophores are highly efficiently quenched by methyl viologen and other known quenchers. We find that quenching efficiency increases with increasing oligomer length and that the efficient quenching can occur with oligomers of varied hydrocarbon fluorophores (pyrene, benzopyrene, or perylene) that display excimer/exciplex excited-state emissions. This suggests that such oligomeric fluorophores may have special utility as reporters and sensors with enhanced sensitivity, both in nucleic acid systems and beyond.

General methods for optical measurements: Absorbance spectra were obtained on a Cary 100 Bio UV-vis spectrometer. Fluorescence studies were performed on a Jobin Yvon-Spex Fluorolog 3 spectrometer. Methyl viologen dichloride hydrate (98%) was purchased from Sigma-Aldrich. The concentration of a stock solution was determined by the measuring the absorbance at 260 nm ($\epsilon$=14,800 cm$^{-1}$). Solutions of 1-14 were prepared to an optical density of 0.05 in distilled water, which corresponds to 2 μM fluorophore monomer concentration, in order to minimize inner filter effects. Perylene in cyclohexane was used as a reference for quantum yields. Quantum yields were calculated according to the equation:

$$\frac{\Phi}{\Phi_R} = \frac{n^2}{n_R^2} \times \frac{\int F}{\int F_R} \times \frac{I_0(\lambda_{ex})}{I_0(\lambda_{ex,R})}$$

where the factor, $I_o(\lambda_{ex})/I_o(\lambda_{ex,R})$ is the correction for lamp intensities at 345 nm (for pyrene) and 450 nm (for perylene).3 Cuvettes utilized for the quenching experiments were treated with hexamethyldisilazane in order to minimize electrostatic interactions between the anionic quartz surface and the cationic MV. The slope of the Stern-Volmer plots were linear over the regions shown for 1-14.

Example 2

Highly Sensitive Oligomer Dye/Quencher Pairs and Their Use in Sensing

The two molecules below were synthesized and purified. One (the top compound) consists of a tetrapyrene excimer fluorophore with a nonfluorescent (tetrahydrofuran) commercial spacer at its 3' end. The second (the bottom compound) contained the same tetrapyrene fluorophore, but with a commercial dabcyl quencher at the 3' end. The fluorescence quantum yield was measured for both in water. The data showed that the molecule with a quencher linked to the oligomeric excimer fluorophore had a quantum yield 1000-fold lower than that of the fluorophore lacking a quencher. The data show that covalent linking of a quencher to an excimer fluorophore yields highly efficient quenching, thus giving a very low background signal. The cleavage of such a linker results in a large increase in fluorescence.

Example 3

Sensors of Esterases and Lipases

An oligodeoxyfluoroside (ODF) oligomer is conjugated to a viologen quencher by a linkage that contains an ester group. The oligomer has the generic structure of Formula I:

A may be present or absent. Where A is present it may be a scaffold group, or a bond or linker to a substrate, which substrate may include a bead, polynucleotide, polypeptide, solid surface, etc.;

X is a scaffold moiety;

R is an excimer or exciplex forming dye, where each R can be the same or different;

n is 0 to 18,

Y is a cleavable linker, and

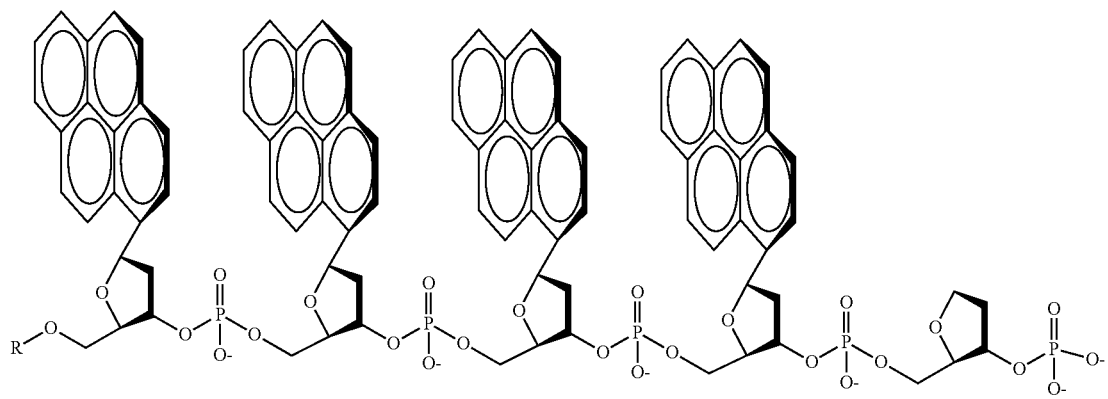

Quantum yield = 0.15

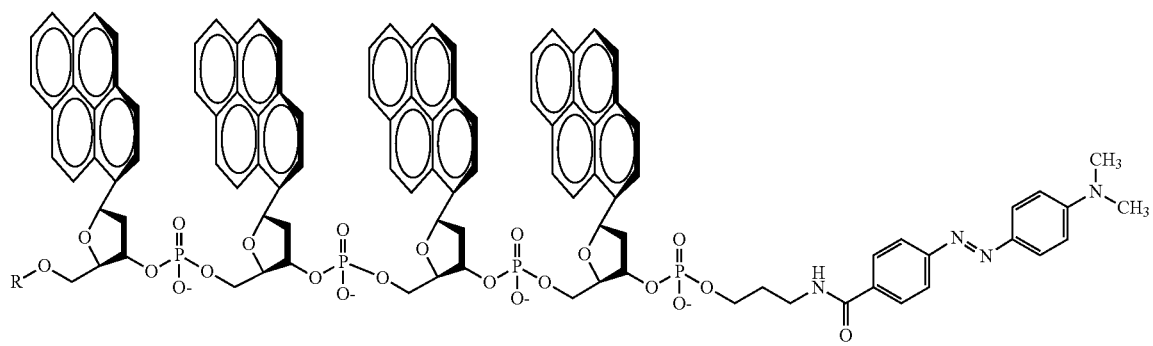

Quantum yield = 0.00015

Z is a quencher for R. Thus, $X_1\text{-}(X_2)_n\text{-}X_3$ is a polychromophoric excimer-emitting or exciplex-emitting fluorophore.

One Example:

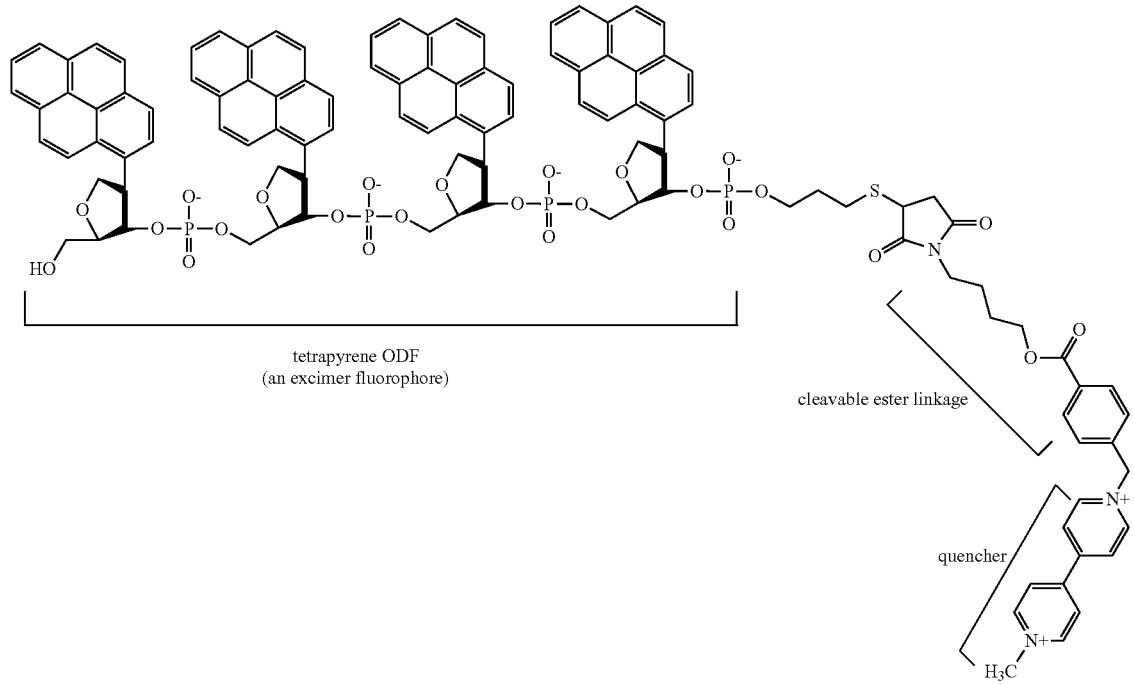

tetrapyrene ODF
(an excimer fluorophore)

cleavable ester linkage quencher

Methods.

A viologen-ester-maleimide conjugate is synthesized, and a tetrapyrene ODF, using a DNA synthesizer. The ODF-thiol conjugate is mixed with the quencher-maleimide conjugate in aqueous buffer and incubated. The product is then separated from unwanted starting materials and products by HPLC.

Solution sensing method. The esterase sensor molecule is dissolved in an aqueous solution containing suspected esterase activity. The esterase activity cleaves the ester linkage, separating the viologen quencher from the tetrapyrene ODF. The concentration of the sensor is in the range of 1 pM to 10 μM. Because the ODF is quenched highly efficiently, the solution has little if any measurable fluorescence prior to esterase action. As the linkage is cleaved, the viologen quencher is separated from the ODF, which becomes brightly fluorescent. This indicates the presence of an esterase activity in the solution. The amount of esterase activity is calibrated by taking a known esterase with the sensor and making a calibration curve with varying concentrations of esterase activity.

Different esterases have different inherent preferences for ester substrate structure. For example, some esterases may prefer longer aliphatic chains than others. To differentiate one esterase from another, different linker lengths are used in different sensors. One sensor can be used to report on the presence of one type of esterase, while another (with a different chain length) can be used to report on a different esterase.

Supported sensing method. In one application, the sensor is conjugated to a glass support or to plastic beads. A solution containing possible esterase activity is added to the beads/glass. If present, the esterase cleaves the cleavable bond, releasing the quencher. In real time, the beads or glass support becomes brightly fluorescent.

In a second application, one end of the oligomeric fluorophore is attached to DNA oligomer 10-40 nucleotides in length, having a known sequence. For example, the specific sensor shown above has DNA sequence at its 5' end; this is attached during synthesis of the tetrachromophore portion, simply by continuing with DNA synthesis on the DNA synthesizer. This sensor-DNA conjugate is added to a commercial DNA microarray on glass or plastic under conditions that allow hybridization to occur.

Cell and tissue sensing method. The sensor molecule is added to cells or tissues, either alone or in the presence of known agents that aid cellular uptake. The sensor molecule enters the cell and an enzymatic activity (such as an esterase) cleaves the cleavable linkage, resulting in a fluorescence signal. This identifies an enzymatic acitivty directly in the cell or tissue by its fluorescence signal, which can be detected by fluorescence microscopy, fluorescence microplate readers, or by flow cytometry.

Example 4

Sensors of Endonucleases

An oligodeoxyfluoroside oligomer is conjugated to the viologen quencher by a linkage that contains at least two DNA units separated by a natural phosphodiester. An endonuclease enzyme (such as S1 nuclease) cleaves this bond, separating the ODF dye from the quencher and yielding a large increase in ODF fluorescence.

Example 5

Sensors of Proteases

An oligodeoxyfluoroside oligomer is conjugated to the viologen quencher by a linkage that contains at least two DNA units separated by a natural amide bond between at least two amino acids. A protease enzyme (such as chymotrypsin) cleaves this bond, separating the ODF dye from the quencher and yielding a large increase in ODF fluorescence.

Example 6

Synthesis and Testing of Dabcyl-Quenched Esterase and Lipase Probes with a Pyrene Excimer Fluorophore Alkyne-quencher compounds 2, 4, and 6 were designed to contain ester groups and a dabcyl quencher group. Compounds 2 and 6 were esters of aryl carboxylates, while compound 4 was an ester of an alkyl carboxylate. The compounds contained terminal alkyne groups for ease of conjugation to the ODF dye, which was designed to contain a 5' azido group. Copper-catalyzed Huisgen reaction ("click chemistry") was then used to react these compounds, each separately, to 5'-azido-C6-YYYYSS (the azide-ODF). C6 refers to a 6-carbon commercial linker between azide and the polyfluorophore. YYYYSS is the sequence of the fluorescent label oligodeoxyfluoroside, where "Y" is a pyrene deoxyriboside monomer and "S" is a nonfluorescent spacer, added to increase water solubility and discourage aggregation.

The 5' azido-C6-YYYYSS was prepared in the following manner. Alpha-pyrene nucleoside phosphoramidite was prepared by the published methods. A C3 spacer phosphoramidite was purchased from Glen Research. Bromohexyl phosphoramidite was also purchased from Glen Research. The sequence 5'YYYYSS was synthesized on controlled pore glass (CPG) solid support using an Applied Biosystems automated DNA synthesizer, and the bromohexyl phosphoramidite was then added as the last coupling step. The bromohexyl sequence was then converted to azidohexyl using the protocol described by Glen Research, treating the sequence with sodium azide in the presence of iodide catalyst. The product was then deprotected using standard ammonia conditions. The resulting azido-C6-YYYYSS (also referred to as the polyfluorophore-azide label) was then purified by reverse phase HPLC.

The following conditions were used to couple the alkyne-quencher to the polyfluorophore-azide label: 5 mM $CuSO_4$, 5 mM sodium ascorbate, 0.5 mM Alkyne Quencher (2, 4, or 6) for 0.02-0.2 mM azide-ODF; usually 2-3 hrs (but up to 48 hr) at room temperature, in 1:1 ratio of $H_2O$/t-BuOH. This resulted in probes 1, 2, and 3, which were purified by HPLC, and characterized by MALDI-mass spectrometry, and by UV absorption (which showed peaks characteristic of pyrene and dabcyl). Fluorescence spectra of the three showed very weak fluorescence, which established that the dabcyl group quenched the YYYY fluorophore very efficiently.

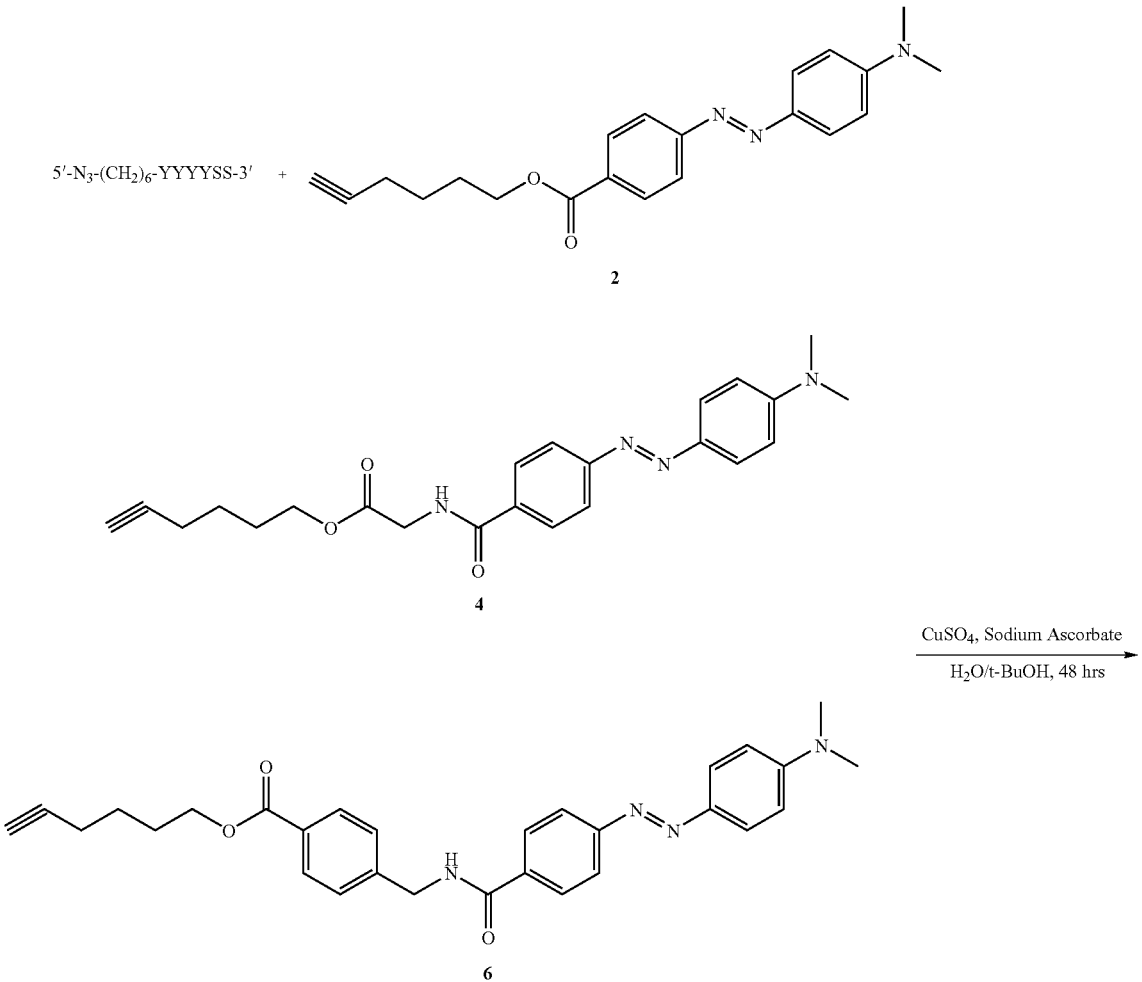

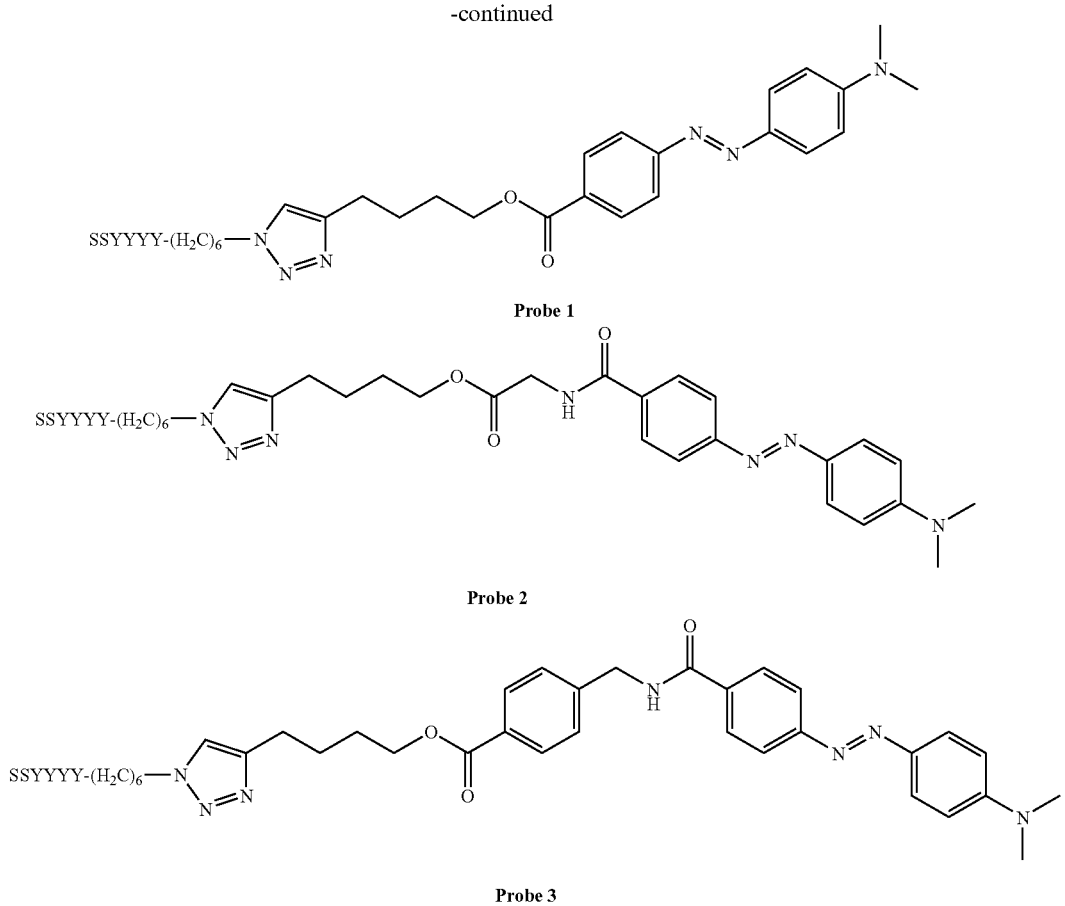

Probe 1

Probe 2

Probe 3

We then used these probes to screen for activity in sensing esterase and lipase activity. We purchased 11 esterases and 10 lipases from commercial sources. These were derived from a variety of organisms (mammals, fungi, and bacteria). Typical screening conditions were: probe 500 nM, enzyme 30 μg/mL at 25° C. in water for up to 18 hr. Excitation was at 340 nm, and emission was monitored at 480 nm.

Figure 3A:
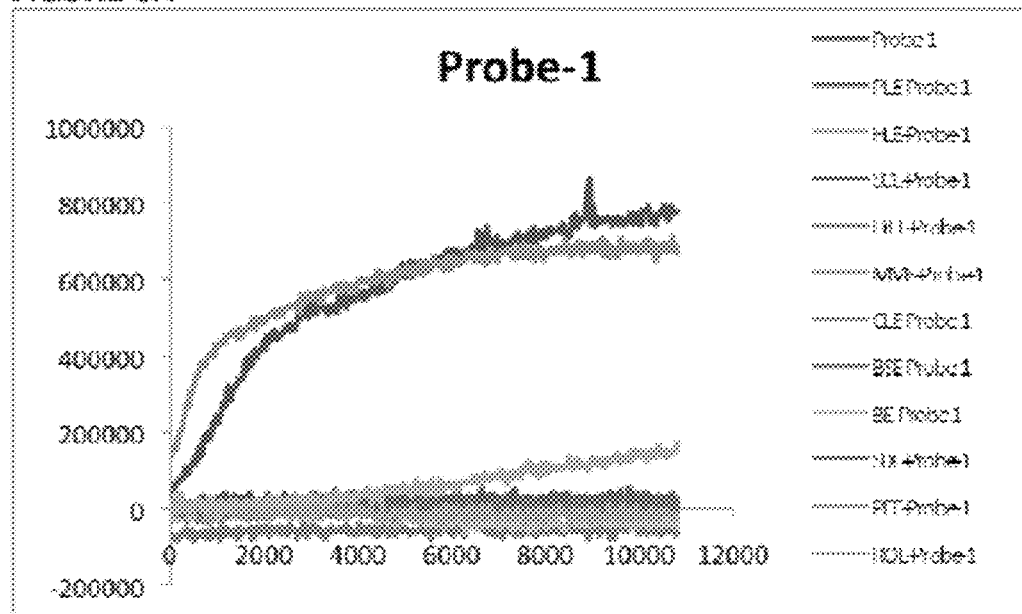
FIGS. 3A-3C. Esterase screens are shown in the plots of fluorescence versus time (in min). Probe: 0.50 µM, Enzyme: 30 µg/mL; Excitation at 340 nm, monitor emission at 480 nm at 25° C. Esterases tested: PLE: Esterase from porcine liver, suspension in 3.2 M $(NH_4)_2SO_4$, 1.22 mg/mL, 171.1 U/mg protein (Sigma E2884); HLE: Esterase from hog liver, 165 U/mg (Fluka 46058); SCE: Esterase from *Saccharomyces cerevisiae*, 2.2 U/g (Fluka 46071); HrLE: Esterase from horse liver, 0.5 U/mg (Fluka 46069); MME: Esterase from *Mucor miehei*, 1.08 U/mg (Fluka 46059); CLE: Esterase from *Candida lipolytica*, 0.10 U/mg (Fluka 46056); BSE: Esterase from *Bacillus stearothermophilus*, 0.47 U/mg (Fluka 46051); BE: Esterase from *Bacillus* species, 0.11 U/mg (Fluka 46062); SDE: Esterase from *Streptomyces diastatochromgenes*, recombinant from *E. coli*, 31.8 U/mg (Fluka 78042); PFE: Esterase from *Pseudomonas fluorescens*, recombinant from *E. coli*, 4.8 U/mg (Fluka 75742); ROE: Esterase from *Rhizopus oryzae*, 66.7 U/mg (Fluka 79208)
Figure 3B:
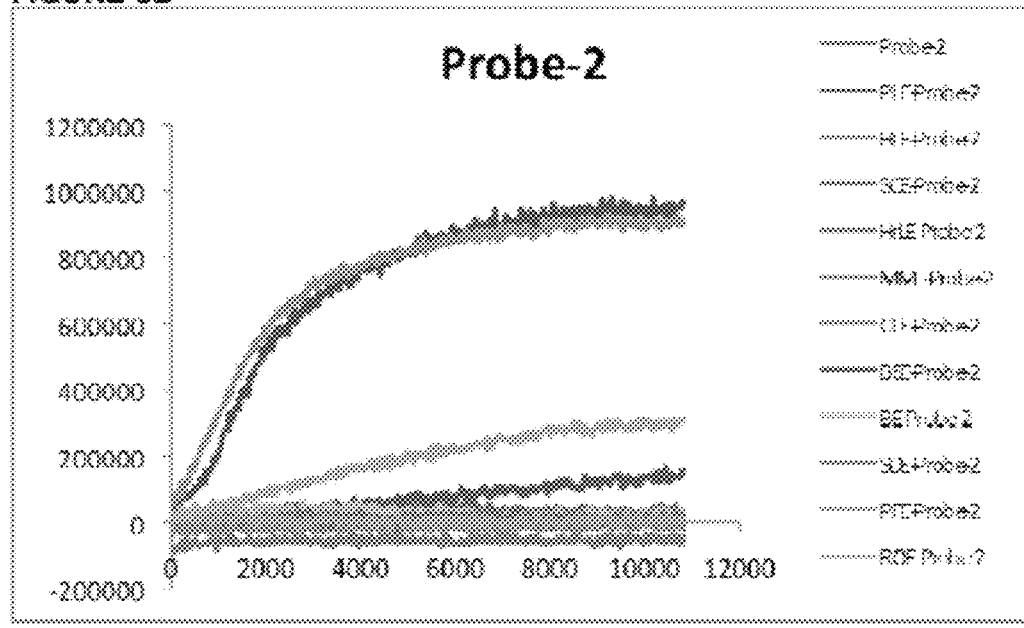
Figure 3C:
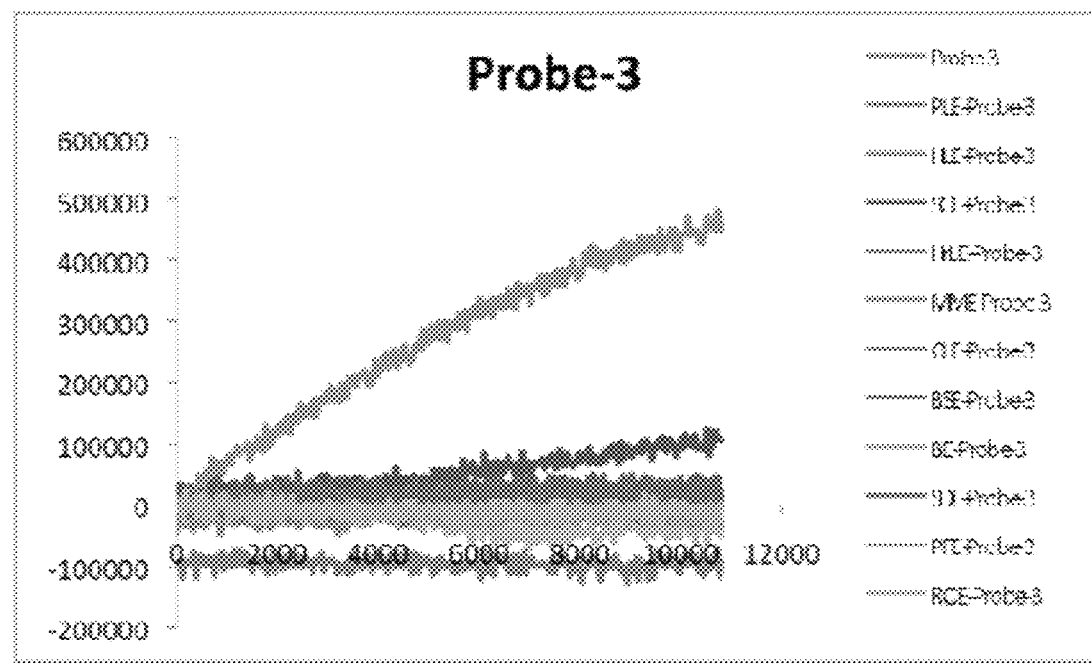

The results from the esterase screens are shown in the plots of fluorescence versus time (in min) in FIGS. 3A-3C. FIG. 3A, probe 1 responded positively to three esterases; FIG. 3B, probe 2 to four esterases, and FIG. 3C, probe 3 to two esterases. In all, four different esterases were detected efficiently by the probes.

Figure 4:
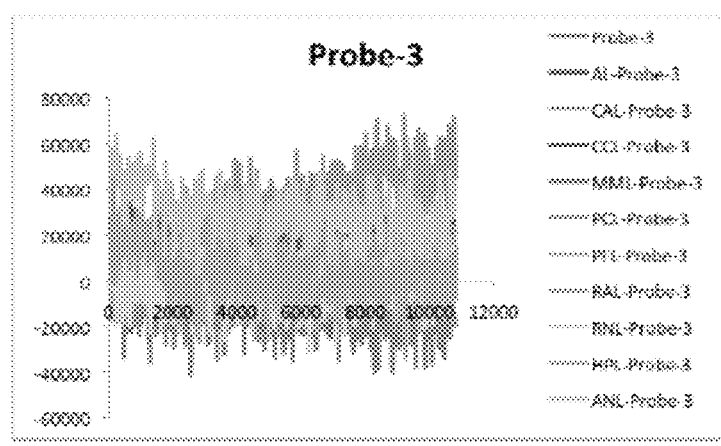
FIGS. 4A-4C. Lipase screening: Probe: 0.50 µM, Enzyme: 30 µg/mL, Excitation at 340 nm, monitor at 480 nm at 25° C. Lipases tested: AL: Lipase from *Aspergillus*, 0.2 U/mg (Fluka 84205); CAL: Lipase from *Candida Antarctica*, 1.51 U/mg (Fluka 65986); CCL: Lipase from *Candida cylindracea*, 4.01 U/mg (Fluka 62316); MML: Lipase from *Mucor miehei*, 1.19
Figure 4:
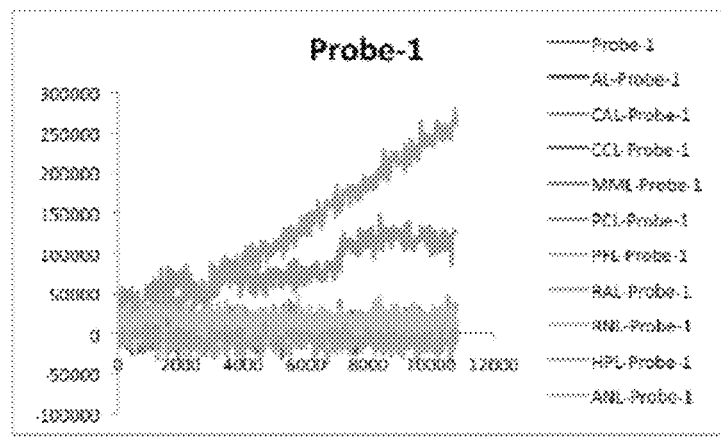
Figure 4:
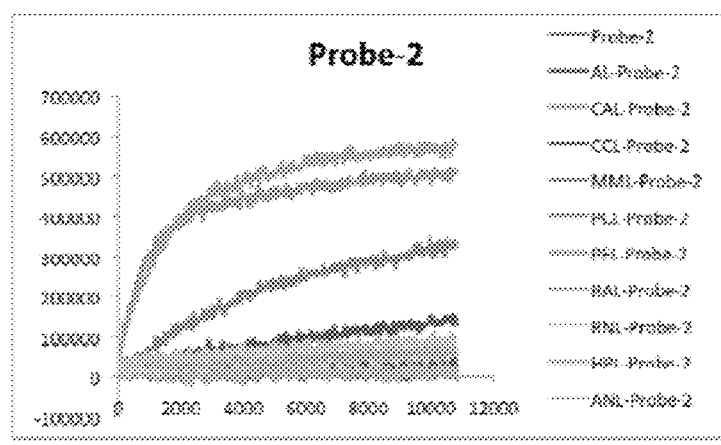

The results from the lipase screens are shown in FIGS. 4A-4C. FIG. 4A, probe 1 responded positively to two lipases; FIG. 4B probe 2 to four lipases, and FIG. 4C, probe 3 slightly responded to one enzyme. In all, ten different lipases were detected by the probes.

We then tested the degree of signal increase by probe 1 with porcine liver esterase (see graph below). Results showed that after reaction, the fluorescence peak at ca. 480 nm had increased in intensity by 109-fold, which is a much larger increase than seen for nearly all previous sensors of esterases. This again established the high degree of quenching possible with the polydfluorophore excimer emission. Importantly, the standard monomeric fluorophore emission increased only by 7-fold. This documents the surprisingly different behavior of excimers and exciplexes in quenching and superquenching by a common quencher group as compared with a standard fluorescent label.

Note that a single pyrene has been used recently in esterase sensors (Y. Yang et al, Organ. Biomol. Chem. 2006, 4, 1746-54). In that design, the authors used a dinitroaniline quencher group with a pyrene label. They found much smaller degrees of quenching (approx. 10-15-fold) as compared with our results. It is surprising that four pyrenes can be quenched better than one, but it reveals the unusual quenching characteristic of the excimer state used in our design.

We took a photograph of a solution of probe 1 in water for 3 days (FIG. 5A) and after treatment with porcine liver esterase (FIG. 5B), again showing the marked signal increase for this probe. Note that the probe is quite stable without enzyme, which has been reported to be a problem with the common commercial esterase sensor dye acetylfluorescein.

We tested probes 1 and 2 for the ability to report on cellular esterase activity. We incubated probes at 5 μM with HeLa cells for 24 hr, washed the cells and took a photomicrograph (FIG. 6). The cells showed clear excimer-colored fluorescence, which compared almost identically with cell labeled with YYYYSS free label. Thus these probes can be used to detect esterase activity both in vitro and in living cells.

This probe design offers a number of advantages over previous esterase (or other bond-cleaving enzyme) probes. First, the sensitivity is higher than nearly all previous approaches, due to the superquenching charateristics of the excimer/exciplex dyes such as YYYY used here. Second, the probes are always water soluble (unlike, for example, the esterase probes of Yang et al.), and thus do not require the addition of cosolvents such as DMSO to dissolve them (and potentially perturb the enzyme). Third, our design allows for trivially easy switching of colors for different applications, as YYYY can be changed to another polyfluorophore sequence; this change is made using the DNA synthesizer. Also importantly, the colors can be used simultaneously with one excitation wavelength and one filter set, allowing the user to visualize multiple enzyme activities simultaneously.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept and scope of the invention. More specifically, it will be apparent that certain agents which are chemically related may be substituted for the agents described herein while the same or similar results would be achieved. All such similar substitutes and modifications apparent to those skilled in the art are deemed to be within the scope and concept of the invention.

What is claimed is:

1. A sensor having the structure:

I wherein A is a backbone group or a linker, and may be absent or present;
X is a backbone group;
R is a fluorochrome, where each R can be the same or different, and wherein at least two R groups are an excimer or exciplex forming fluorochrome;
n is 2 to 20,
Y is a cleavable linker, and
Z is a quencher for R, wherein Z quenches with a Stern-Vollmer constant ($K_{sv}$) of greater than $10^6 M^{-1}$, wherein the increase in fluorescence, following cleavage of the quencher, is at least about 20-fold.

2. The sensor of claim 1, wherein the increase in fluorescence is at least about 100-fold.

3. The sensor of claim 1, wherein X is a phosphodiester, phosphorothioate, phosphotriester, locked nucleic acid (LNA); morpholino; 2'-O-methyl RNA, or peptide nucleic acid.

4. A sensor having the structure:

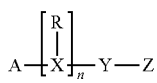

I wherein A is a backbone group or a linker, and may be absent or present;
X is a backbone group;
R is a fluorochrome, where each R can be the same or different, and wherein at least two R groups are an excimer or exciplex forming fluorochrome;
n is 2 to 20,
Y is a cleavable linker, and
Z is a quencher for R, wherein R is selected from pyrene, perylene, benzopyrene, oxoperylene, rubrene, perylene bisimide, styrene, anthracene, tetracene, pentacene, and fluorene.

5. The sensor of claim 1, wherein Z is selected from methyl viologen, methyl red, dabcyl, dabsyl, dansyl, FRET acceptors, TAMRA, Iowa black, nitroxyl quenchers, black hole quenchers, dimethylaminostilbene, dimethylaminoazobenzene, dimethylaniline, nitrobenzene, pentafluorobenzene, methylpyridinium, and phenyl-(methylpyridinium).

6. The sensor of claim 1, wherein Y is directly or indirectly cleavable by an analyte selected from lipase, esterase, nuclease, peptidase, glycosidase, metal catalyst or environmental condition.

7. The sensor of claim 1, having homogenous R groups.

8. The sensor of claim 1, having mixed R groups.

9. The sensor of claim 1, linked to a substrate through A.

10. The sensor of claim 1, linked to a member of a specific binding pair through A.

11. A method for detection of an analyte of interest, the method comprising:
contacting a sample suspected of comprising said analyte of interest with the sensor according to claim 1, wherein Y is directly or indirectly susceptible to cleavage by the analyte; and
measuring the fluorescence of the sample.

12. The sensor of claim 1, wherein Y comprises a chain of less than about 30 atoms in length, wherein said chain comprises a cleavable bond; and one or more of an amide, a thioether and a triazole.

13. The sensor of claim 12, wherein Y is of the structure:

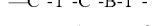

wherein $C^1$ and $C^2$ are each independently a chain of about 2 to 6 atoms in length;
wherein $T^1$ is selected from a thioether group, a triazole group, and an amide group;
wherein $T^2$ is selected from a single bond, a chain of about 2 to 6 atoms in length, an aminomethylene group, an aminomethylphenyl group, and a benzyl group; and
wherein B is a cleavable bond.

14. The sensor of claim 1, wherein X is a phosphodiester such that the backbone groups Xn comprise a deoxyribose-phosphate backbone.

15. A sensor having the structure:

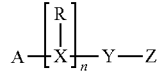

I wherein A is a backbone group or a linker, and may be absent or present;
X is a backbone group;
R is a fluorochrome, where each R can be the same or different, and wherein at least two R groups are an excimer or exciplex forminq fluorochrome;
n is 2 to 20,
Y is a cleavable linker, and
Z is a quencher for R, wherein Z quenches with a Stern-Vollmer constant ($K_{sv}$) of greater than $10^6 M^{-1}$.

* * * * *